US005593389A

United States Patent [19]

Chang

[11] Patent Number: 5,593,389
[45] Date of Patent: Jan. 14, 1997

[54] URETHRAL CATHETER HOLDER WITH ANCHORING DEVICE

[76] Inventor: Hau H. Chang, 7704 Calle Espada, Bakersfield, Calif. 93309

[21] Appl. No.: 452,663

[22] Filed: May 25, 1995

[51] Int. Cl.$^6$ ............................................. A61M 5/32
[52] U.S. Cl. ................... 604/174; 128/DIG. 26; 604/349; 604/177
[58] Field of Search ................ 128/DIG. 26; 604/167, 604/171, 172, 174, 175, 179, 180, 349, 351, 353, 355, 177, 265

[56] References Cited

U.S. PATENT DOCUMENTS

| | | | |
|---|---|---|---|
| 4,397,647 | 8/1993 | Gordon | 604/180 |
| 4,498,903 | 2/1985 | Mathew | 604/179 |
| 4,699,616 | 10/1987 | Nowack et al. | 604/180 |
| 4,710,169 | 12/1987 | Christopher | 604/265 |
| 4,897,082 | 1/1990 | Erskine | 604/177 |
| 5,069,206 | 12/1991 | Crosbie | 604/174 |
| 5,226,892 | 7/1993 | Boswell | 604/180 |

*Primary Examiner*—Sam Rimell

[57] ABSTRACT

Urethral catheter holder with anchoring device is a device that has two semicylindric elements connected together by a flexible living hinge on one edge and a single non adjustable male and female locking tooth on the other edge opposite to the living hinge. It has two semi-cylindrical rim extensions at one end of the device that extend to a diameter larger than said semicylindric elements. There is a compressible foam pad lining the inner surface of the semicylindric elements. The rim extension for male use is taller than that for female use and is lined with a layer of foam pad impregnated with antimicrobial agent. Each of the foam pad on the rim extension in the female use device is made half of a doughnut shape and is impregnated with antimicrobial agent. There is a wedge defect on the rim extension at the living hinge side and is covered by a curve extension. In a male use device, there is(are) a single or double telescoping condom(s) with both ends opened and a slit on one side of the condom(s). In a female use device the condom is substituted with a perineal shield or the anchoring straps may directly attach to the outer edge of the rim extension. The anchoring straps in both the male and female devices further attach to a waist belt.

3 Claims, 8 Drawing Sheets

5,593,389

URETHRAL CATHETER HOLDER WITH ANCHORING DEVICE

BACKGROUND OF THE INVENTION

1) Field of the invention

The invention relates to a device that can be clipped on the urethral catheter immediately external to the male and female urethral meatus after the catheter is inserted while using the straps attached to the catheter holder to anchor it on the patient's waist so that the draining position of the catheter can be maintained. Single or double layers of condom rubber dressing is provided between the catheter holder and the straps anchoring points around the penis in the male to assist in stabilizing the catheter in alignment with the male urethra to prevent the catheter tip from slipping out of the urethra since there is a mobile portion of penile urethra between the urethral catheter holder and base of the penis. A device suitable for female use consists of a urethral catheter holder with a shorter rim extension. The rim extension is padded with a donut shaped air filled cushion or foam pad impregnated with antimicrobial agent to minimize trauma to the urethral meatus and provide an antiseptic to reduce nosocomial urinary tract infection. There may or may not be a pliable perineal shield extending outwardly from the rim extension of the catheter holder. The perineal shield is the female counter part of the fixation device that is the condom in the male. The present device is an improvement of my original invention patent number 5,368,575 for different purpose. The basic function and usage of the present invention is to provide means of fixation to the Foley catheter with the balloon deflated in the patient who has been confused and tends to pull the Foley catheter involuntarily, to prevent trauma to the urethra while maintaining the antiseptic means to prevent catheter associated urinary tract infection. The stadium shape rim extension of the catheter holder provides a housing space for the male urethral meatus and antiseptic to be in direct contact without exposure. The foam pad within the catheter holder permits a smooth grip to a Foley catheter without compromising the lumen of the Foley catheter and inflation and deflation tube of the balloon.

Dissimilar to the conventional external condom and its catheter with an extended tube for the draining bag, present invention is designed to fix the indwelling urethral catheter, not the external non indwelling urethral catheter, in place without the balloon inflated within the urinary bladder.

2) Description of the Prior Art

Many patients whether they are admitted to acute care in the hospital or the Skilled Nursing Facility wear a Foley catheter either on a long term or a short term basis. A balloon of the Foley catheter is usually inflated in the urinary bladder to maintain it's draining condition in the body. Many patients become confused while they are acutely ill. Foley catheters are frequently pulled out by themselves with the balloon inflated. Profuse urethral bleeding frequently results, conventional management usually consists of restraint by applying a mitten on their hands and strapping them on the bedsides or taping the urethral catheter on the penis. Nevertheless, the confused patient invariably manages to pull the catheter out prior to the awareness of the nurses. Ascending urinary tract infection frequently occur through urethral meatus within a few days after the Foley catheter is inserted. The antiseptic ointment such as Neosporin (Neomycin Sulfate-Polymyxin B Sulfate) or Betadine (Providone-Iodine) ointment are routinely applied to the external urethral meatus to lubricate the urethral mucosa and to prevent ascending urinary tract infection in anyone who wears the indwelling Foley catheter in the present practice. However, the ointment will soon be removed by the covering linen or patient's underwear and become air dry without proper covering protection, and ascending urinary tract infection through contamination to external urethral meatus soon follows.

SUMMARY OF THE INVENTION

The urethral catheter holder and its associate fixation device consists of a short segment of the tubular structure, condom(s) or perineal shield and anchoring straps. The catheter holder itself is a pair of semicylindric elements. It has a concave half stadium rim extension on one end. One edge of each element is hinged together by a living hinge or web. The other edges can have a non-adjustable male and female locking tooth. The inner surface of the semi-cylindrical short segment catheter holder is covered by a layer of compressible foam pad. The foam pad lining of the extension rim is impregnated with antimicrobial agent such as Neosporin (Neomycin Sulfate-Polymyxin B Sulfate) or Betadine (Providone-Iodine). The device suitable for male patient use has longer rim extension and a single or double layers of condom dressing between the rim extension of the catheter holder and the anchor ends of the straps. The condom is made of a pliable material, it is a tubular structure with both ends opened and a slit on one side of the condom. The distal end of the condom(s) is (are) attached circumferentially to the rim extension of the catheter holder. The slit(s) on the side of the condom(s) is (are) aligned with the locking mechanism of the urethral catheter holder. The circumference of the proximal end of the condom(s) anchoring to the straps is (are) made longer so that when it is applied on the patient's penis it can be overlapped. The slit edges of the condom(s) are mounted with a velcro or adhesive agent so that when the condom(s) dressing is fitted onto or removed from the penis it can be adhered and easily removed from the corresponding edges of the condom dressing. There are four straps attached at equal distance from each other on the proximal end of the condom (or outer condom in the case of double condoms) opposite to the rim extension attachment. The other ends of the four straps are attached to the heavy belt that goes around the waist of a patient. In the case of double condoms, the inner and outer condoms are anchored with each other at their proximal ends opposite to the rim extension attachment at three locations. A scrotal support can be constructed behind the condom(s). The anterior aspect of the upper edge of the scrotal support is attached to the posterior edge of the proximal aperture of the outer condom. In this case, the distal end of the two posterior or middle anchoring straps attached to the posterior aspect of the upper edge of the scrotal support instead to the posterior aspect of the upper aperture of the outer condom.

In the case of a female use urethral catheter holder for said purpose as stated in the field of the invention, the stem of the catheter holder is essentially the same as in the male use device. The differences are on the rim extension and its foam pad and perineal shield. In the female use device the rim extension is shorter, it contains a semilunar foam pad or air filled mattress impregnated with antimicrobial agent on each half of the rim extension. When assembled it forms a donut shaped cushion. There may or may not be an angled extension of the foam pad or the donut shaped air filled mattress from each side of the semilunar foam pad on the living hinge side to assist the fixation of the semicylindric segment of the catheter holder and to prevent the outward migration and displacement of the urethral segment of the Foley catheter. There may or may not be a shield surrounding the outer edge of the rim extension. The shield is a circular or oval shape of pliable soft rubber or cloth related material. There is a central opening of the perineal shield to accommodate the rim extension of the catheter holder. The inner edge of the shield is anchored to the outer edge of the rim extension circumferentially. There is a complete or incomplete slit on the shield aligned with the locking mechanism of the stem of the catheter holder. The slit runs perpendicular to the tangential line of the central opening at the point of the locking mechanism. In the case of a complete slit, the slit traverses the entire width of the perineal shield. There are male and female hooks on either edge of the slit for engagement and disengagement. One end of the four straps are anchored equadistantly from each other on the outer edge of the shield. The opposite ends of the straps are anchored on the heavy waist belt.

The function of the shield in this case is to provide a buffer to the difference in strength of each straps to prevent migration of the intraurethral segment of the catheter from the urethral meatus. In the case of the device without the shield, the four straps are anchored directly at the outer edge of the rim extension at equal distance.

The objective of the present invention is to resolve some of the problems and difficulties in current medical and urological practices. Many patients being treated in the hospitals or skilled nursing facilities wear a Foley catheter for one reason or another. A balloon at the end of the Foley catheter is usually inflated in the urinary bladder to maintain its indwelling position. Elderly patients frequently become confused and traumatize themselves by pulling the Foley catheter with balloon inflated. To minimize the urethral laceration a special device suitable for holding the Foley catheter in position in male and female patients is necessary. The balloon of the Foley catheter is deflated and the external fixation device as outlined above is provided. Consideration is taken not to obstruct or distort the lumen of the Foley catheter or inflation and deflation tube of the balloon in case the balloon needs+ to be inflated again. Means to prevent catheter associated urinary tract infection is provided. The unique features of the present device that set it apart from the conventional medical tube fitment device are: 1) There is a simple non adjustable locking tooth. It is easy to engage and disengage. 2) Compressible pad of the catheter holder produces a round constant symmetrical tubular space in the center of the device to accommodate the urethral Foley catheter of various sizes without distorting configurating or narrowing the lumen of the Foley catheter and its inflation and deflation tube of the balloon. It allows the irrigation fluid, debrides, sediments and small blood clots to flow freely. 3) Because of the smooth grip of the urethral catheter holder to the Foley catheter, the inflation and deflation tube of the balloon remains patent. The Foley catheter balloon can be re-inflated once patient's mental condition became clear. 4) A housing space is provided to antimicrobial agent and both male and female genital organs for comfort and reducing catheter associate nosocomial urinary tract infection. 5) A condom (or condoms) or a shield tailored to the shape of male external genitalia and female perineum to stabilize the catheter and buffer the difference in the strength in each four straps creates a superior adhering anchoring effect for a non balloon inflated catheter to the mobile pendulous urethra in the male and short urethra in female.

BRIEF DESCRIPTION OF THE DRAWING

The urethral catheter holder with anchoring device suitable for the male and the female patient's use in according with the present invention will now be described by way of example with reference to the accompanying drawing.

FIG. 1 is an external side view of the distal portion of the present device suitable for male patient use.

FIG. 2 is a longitudinal section view of the distal portion of the present device suitable for male patient use.

FIG. 3 is an external top view of the distal portion of the present device suitable for male patient use.

FIG. 4 is a three dimensional view of the distal portion of the present device suitable for male patient use.

FIG. 5 is the magnification view of the locking mechanism of the distal portion of the present device suitable for male and female patient use.

FIG. 6 is a three dimensional external view of the distal portion of the present device suitable for male patient use showing rim extension covering the wedge defect.

DESCRIPTION OF THE PREFERRED EMBODIMENT

Figure 1:
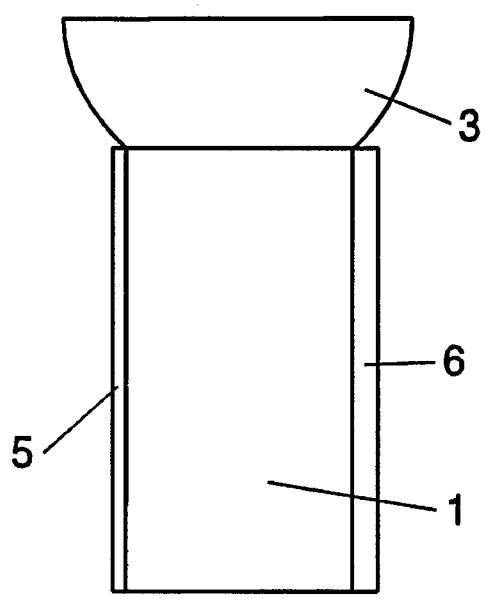
FIGS. 1, 2, 3, 4, 5 and 6 are essentially the same as my previous invention in patent number 5,368,575.
Figure 2:
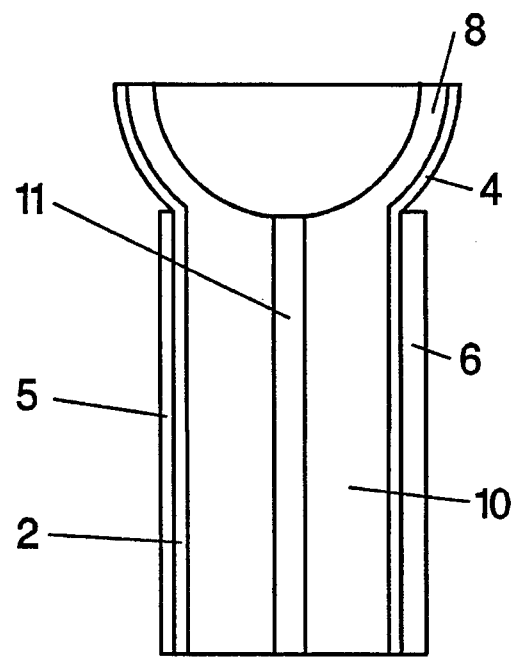
Figure 3:
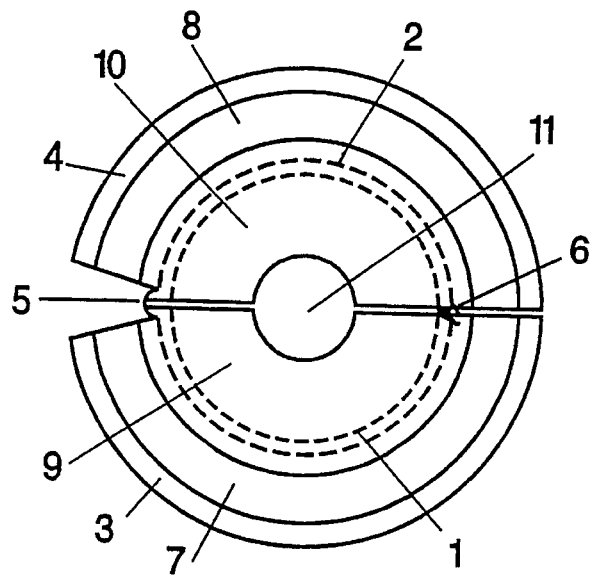
Figure 4:
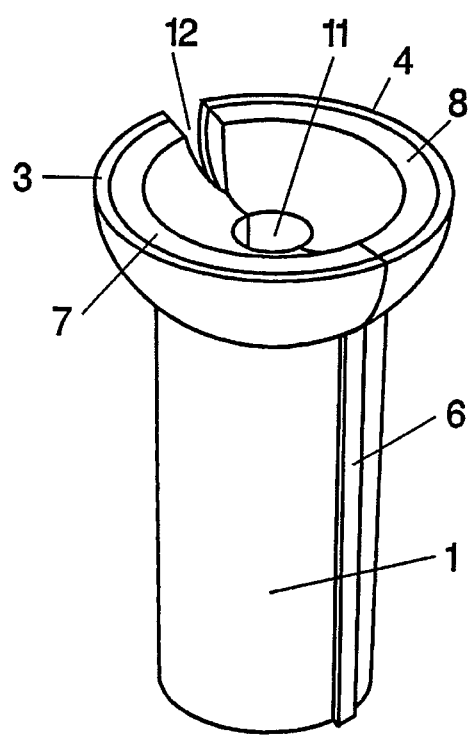
Figure 5:
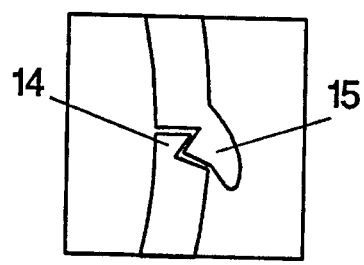
Figure 6:
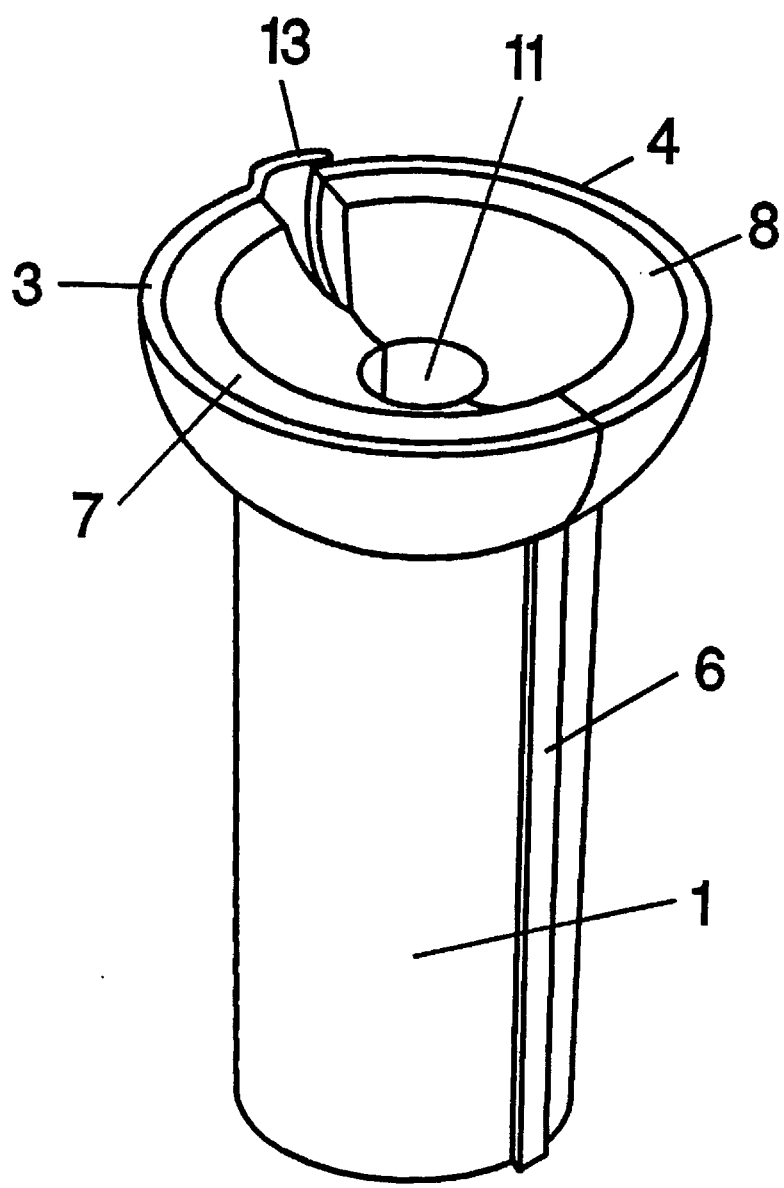

Referring to FIGS. 1, 2, and 3 an embodiment of the distal portion of the urethral catheter holder with anchoring device, the outside view, inside view and top view suitable for male patient use are illustrated. The distal portion of the device consists of two parts, Part (1) & (2). Each of these is half of a segment of a tubular structure, when assembled they form a cylindric tube with a lumen in the center. Within the lumen there are foam pads, (9) & (10). There are concave shaped rim extensions (3) & (4) at one end of the catheter holder. The inner surface of rim extensions are also padded with foam pads, (7) & (8). A tubular space (11) in the center of the foam pad is created to accommodate the Foley catheter. The semi-tubular elements (1) & (2) are hinged together by a living hinge or a web (5's). The other side edges, (6's) can be snapped together as shown in FIGS. 3, 4, 5 & 6. FIG. 5 is a magnification of the cross section view of the locking mechanism at edges, (6's). (15) is the male locking mechanism, (14) is the female locking mechanism. Foam pads on the rim extension (7) & (8) are impregnated with antimicrobial agent (such as Neomycin Sulfate-Polymyxin B Sulfate and Povodine-Iodine). There is a wedge defect on (3), & (4) edges to allow the (1) & (2) elements to open at (6) edges for inserting the Foley catheter into the lumen (11). In order to keep antibiotic ointments and glans penis more in close space within the stadium shape rim extension, a curve extension (13) of rim (3) is made to cover the wedge defect (12) as shown in FIG. 6. The glans penis should be pulled back during the application or removal of the catheter holder to avoid the injury.

Figure 7:
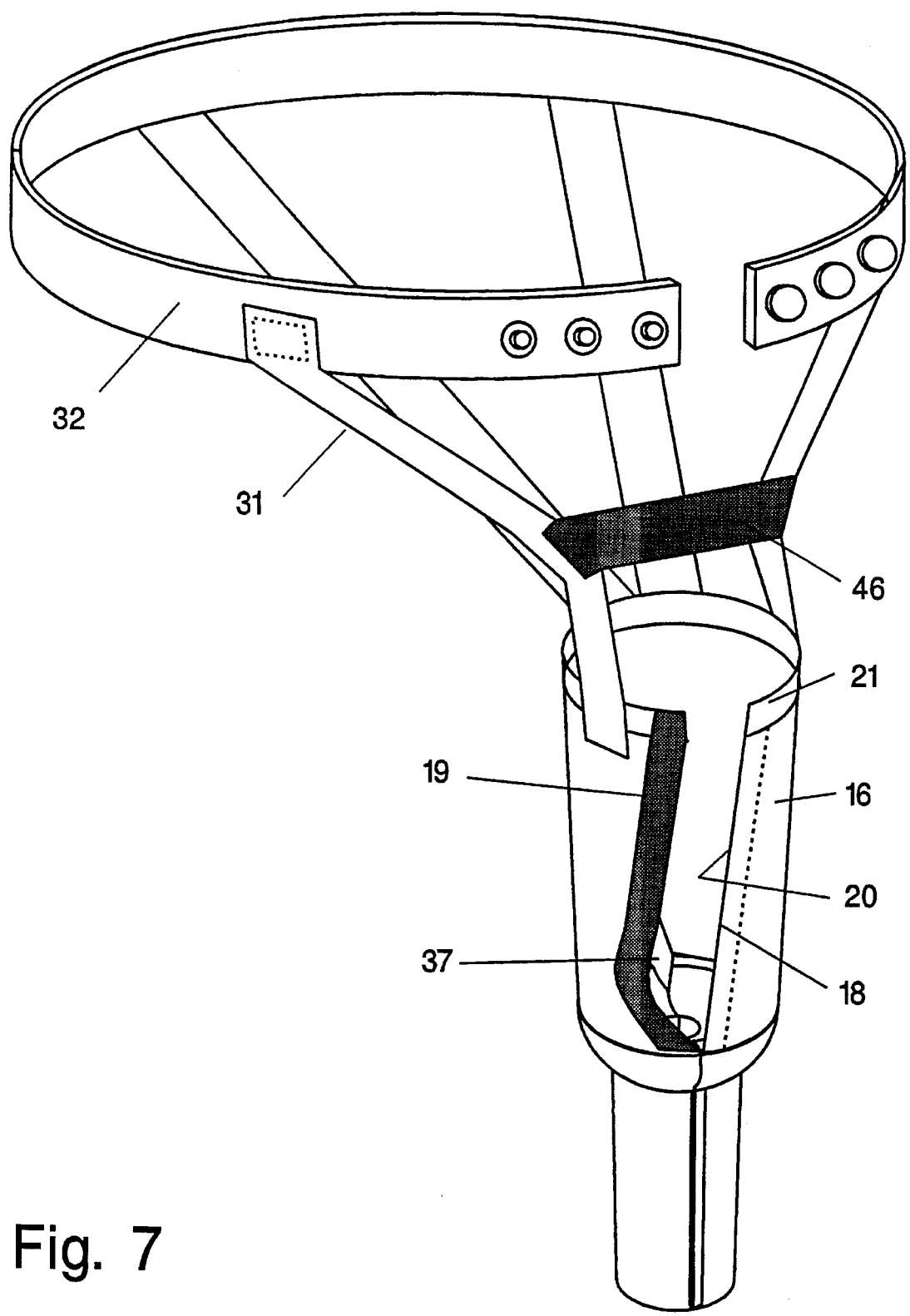
FIG. 7 is a three dimensional external view of the whole device of the present invention suitable for male patient use showing the single condom with the slit opened.
Figure 8:
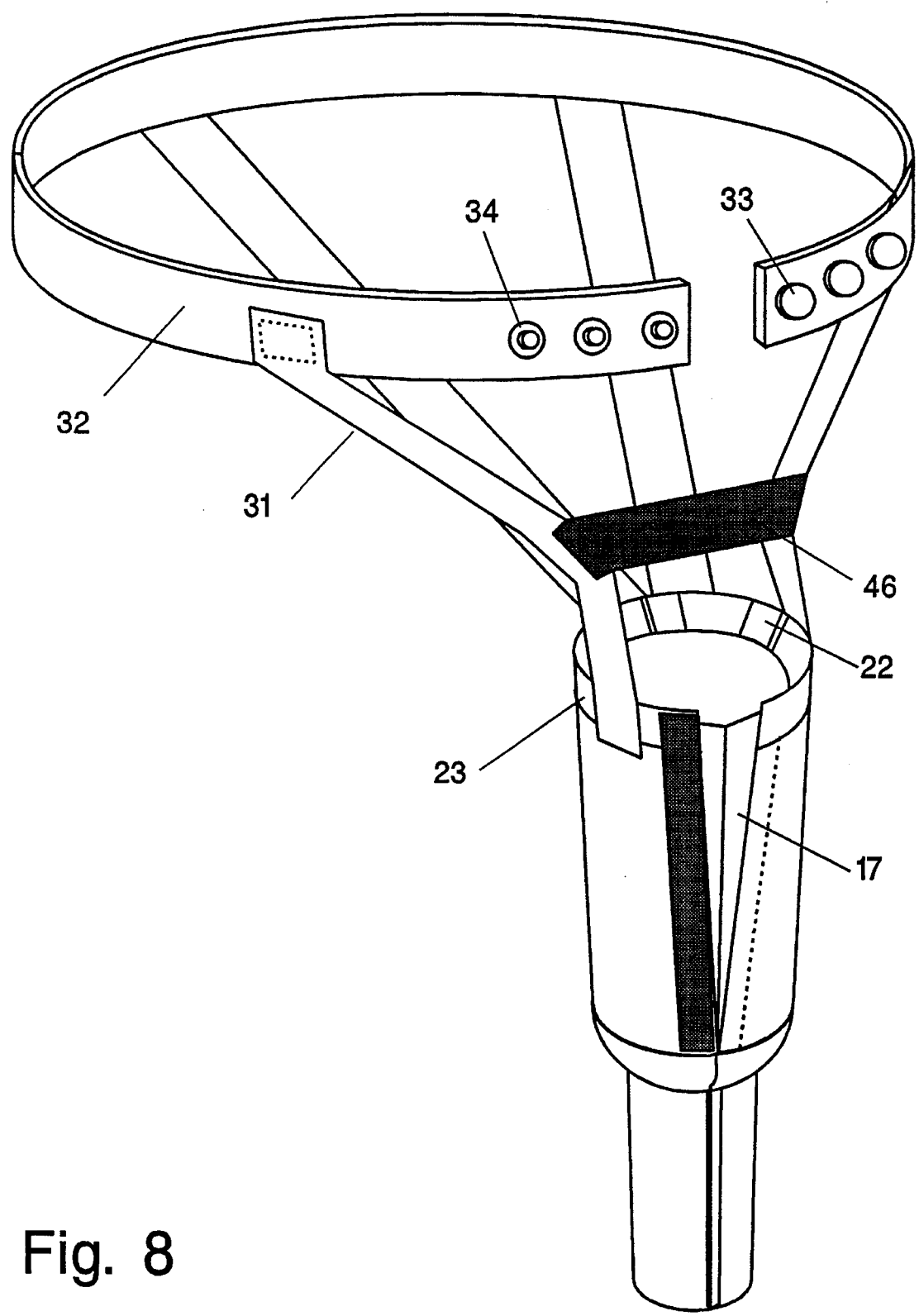
FIG. 8 is a three dimensional external view of the whole device of present invention with double condoms suitable for male patient use. Showing the inner condom closed and the outer condom opened.

Referring to FIG. 7, a single condom (16) is illustrated inserted between the male urethral catheter holder (1, 2, 3 & 4) and the anchoring straps (31), (18's) represent the edges of the slit opening of the condom. Rims of velcro or adhesive area (19) and (20) are provided at the outer and inner surface of each edge of the condom. Therefore, both edges can be re-approximated. In the case of double condoms as illustrated in FIG. 8, three suspensory bridges (22's) are provided to anchor the proximal end of the inner condom (17) to the outer condom (16) to ensure upward standing of the inner condom. Each of the anchoring straps (31) in FIG. 7 & 8 are anchored on the proximal edge of the outer condom opposite to the catheter holder cylinder at equal distance from each other on one end. The straps (31) are further anchored to the waist belt (32) on the opposite end. The proximal end of the outer condom (21) is made thicker and heavier for the purpose of increasing strength for suspension. The distal end of the condom has a aperture the same diameter as the rim extension. The distal end aperture of the condom adheres circumferentially to the outer edge of the rim extension. In the case of the double condom device, the edges of the slit opening of the inner condom also have a rim of adhesive areas for the edges of the inner condom to stick to each other similar to that of the outer condom. Each end of the waist belt (32) has an adjustable male and female anchoring device (33) & (34).

Figure 12:
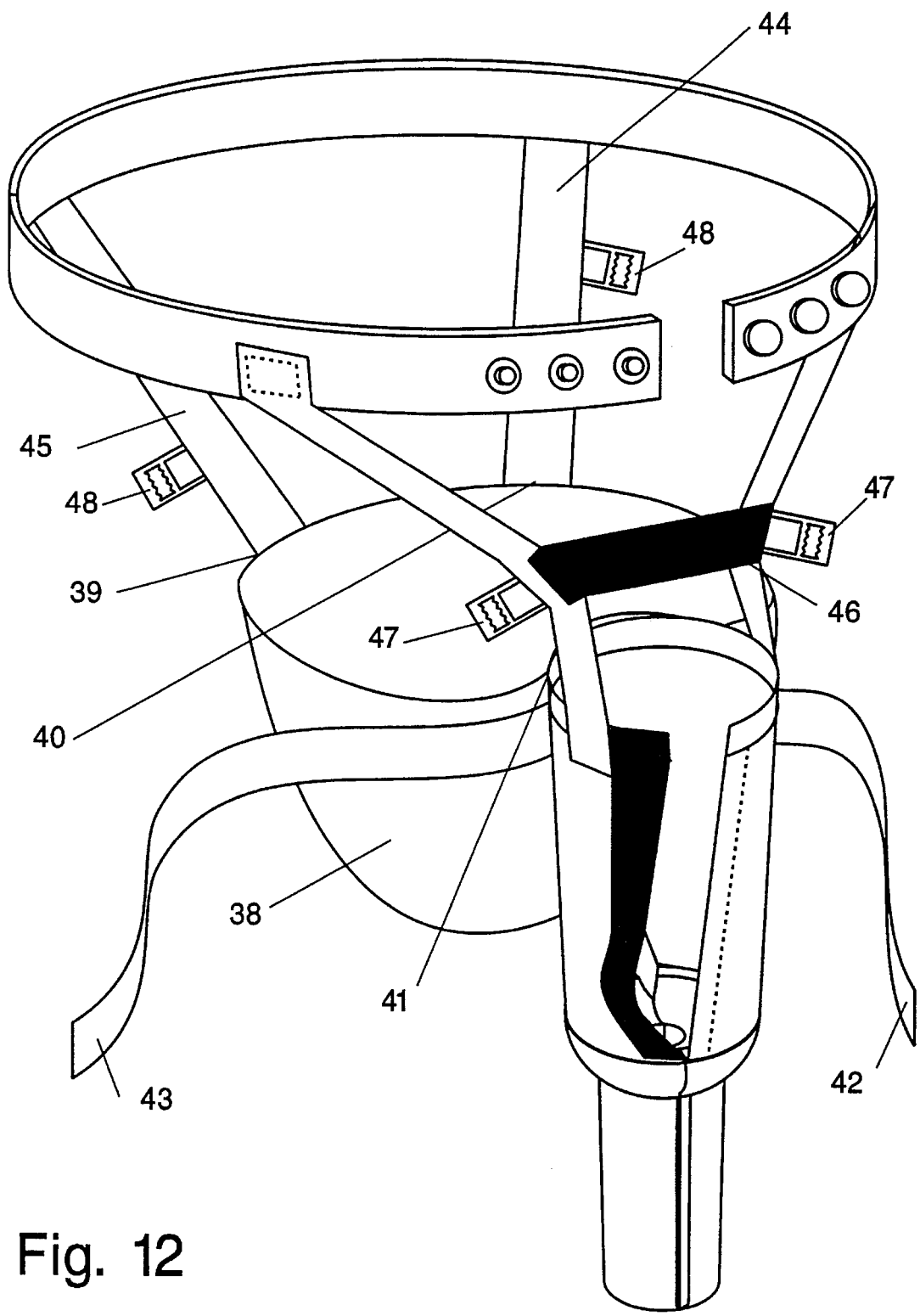
FIG. 12 is a three dimensional external view of the male use device showing the scrotal support behind the condom.

Referring to FIG. 12, a scrotal support (38) may be constructed behind the outer condom in the male use device. In this case, the anterior aspect of the upper edge of the scrotal support is attached to the posterior aspect of the upper aperture of the outer condom at the attaching line (41). The distal end of the two posterior anchoring straps (44 & 45), instead of anchoring to the posterior aspect of the proximal aperture of the outer condom, anchors to the posterior aspect of the upper edge of the scrotal support at (39 & 40). Two additional straps (42 & 43) arises from either side of the lateral aspect of the junction of the scrotal support and the posterior edge of the upper aperture of the outer condom (41) may either terminate to the mid portion of the posterior straps of the scrotal support (44 & 45) at (48 s) or anteriorally to the mid portion of the anterior straps of the condom immediately at the lateral aspect of the commissure of the anterior straps (46) at (47 s).

Figure 9:
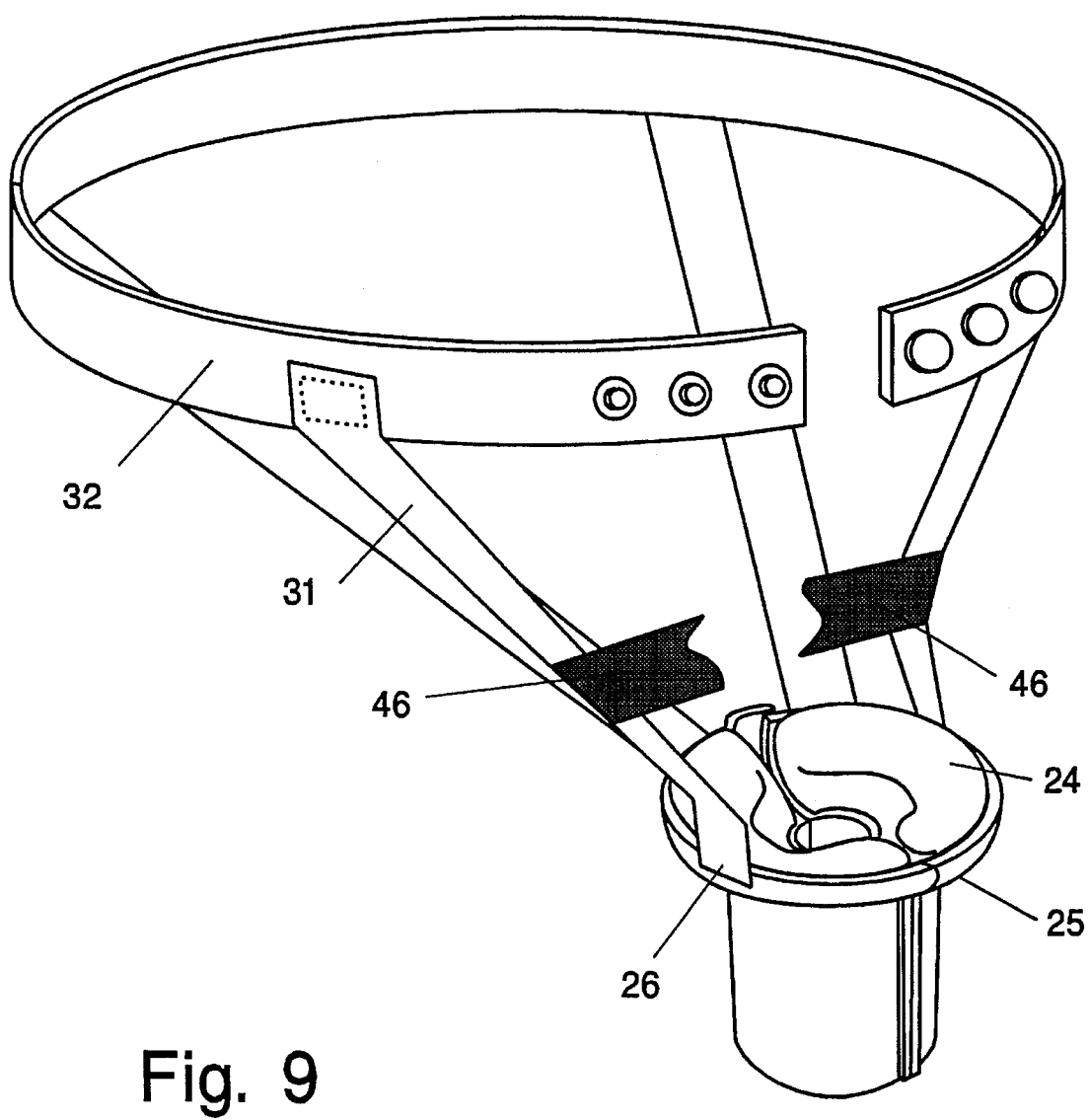
FIG. 9 is a three dimensional external view of the present device without perineal shield suitable for female patient use showing a cushion mattress placed on the shallow stadium extension.

Referring to FIG. 9, an external view of a female urethral catheter holder and its anchoring device without a perineal shield is demonstrated. The structural design of the catheter holder is essentially the same as that of the male urethral catheter holder except the rim extension of the urethral catheter holder (25) is shorter and shallower and each of the cushion foam pads or the air filled mattresses (24) is half moon shape and bulging outwardly. When assembled it forms a donut shaped mattress to buffer the trauma to the urethral meatus, the anchoring straps (31's) are anchored to the rim extension (25) directly at the (26's).

Figure 11:
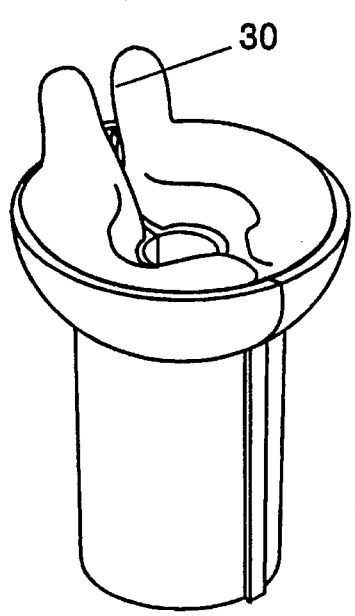
FIG. 11 is a three dimensional external view of the distal portion of the present device suitable for female patient use showing a protrusion of the cushion to stabilize the catheter on the urethral meatus.

Referring to FIG. 11, vertical angled protusions of the foam mattresses (30)s are constructed at the wedge defect of the rim extensions of the semi cylindric elements of the catheter holder to assist stabilized the semi cylindric element and the catheter in position at the urethral meatus of a female patient.

Figure 10:
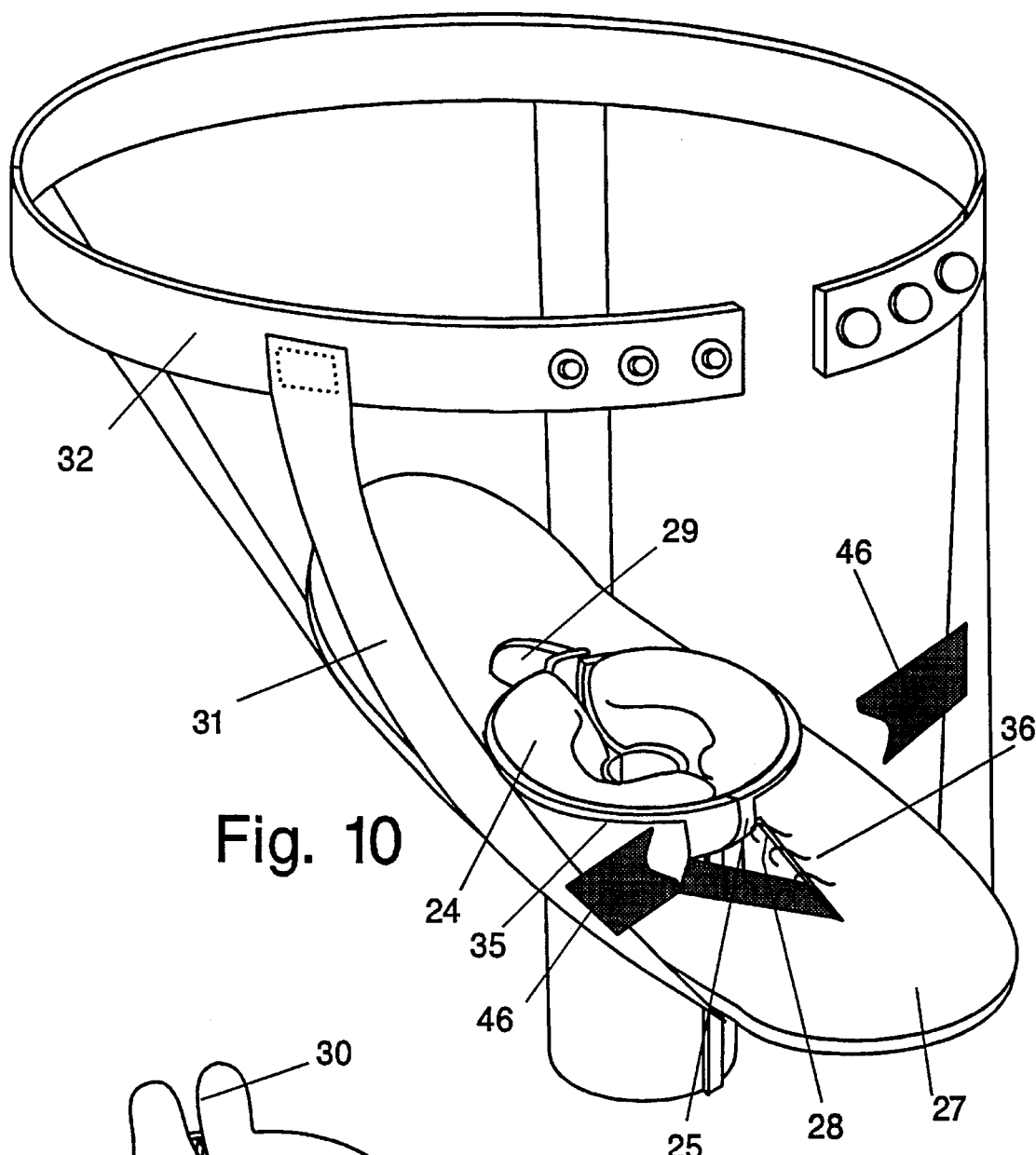
FIG. 10 is a three dimensional external view of the present device with an oval shape shield for female patient use showing a cushion mattress placed on the shadow stadium extension and an oval shield molded to the shape of the perineum.

Referring to FIG. 10 external view of a female urethral catheter holder with an oval shape perineal shield and anchoring device is illustrated. (27) represents a soft pliable rubber or cloth like perineal shield. The upper surface of the perineal shield is padded with a layer of sanitary absorbent similar to conventional sanitary pad. There is an opening in the center of the perineal shield. The edge of the central opening (35) is directly attached to the upper edge of the rim extension (25). The size and shape of the perineal shield varies from large to small and circular, oval to spindle shapes. A slit (28) perpendicular to the circumference of the central opening (35) is created on the perineal shield extending from the central opening of the shield at the locking mechanism side of the semicylindrical element partially or completely through the width of the perineal shield. The slit edges have re-approximate hooks, (36). A semicircular or a slit defect (29) is created on the perineal shield besides the living hinge side of the rim extension said semicircular defect on the perineal shield is confluent with the central opening of the said shield in the female use device. A similar small opening (37) as shown on FIG. 7 is also created on the condom adjacent to the living hinge side of the rim extension in the male use device. Referring to FIGS. 7, 8, 9, 10, & 12, there is a fixation commissure (46) to stabilize the anterior straps adjacent to the slit of the condom in the male use device and the slit of the perineal shield in the female use device. Although detailed embodiments of the invention are illustrated in the drawings and previously described in detailed. This invention contemplates any configuration, dimension, design and relationships of components which will function in a similar manner and which will provide the equivalent result.

I claim:

1. A urethral Foley catheter holder and anchoring device for supporting the Foley catheter holder in a urethral meatus comprising:

a) a first short semicylindrical segment with a semicylindrical rim extension at one end that extends to a diameter larger than said short semicylindrical segment, said short segment comprising a foam pad lining an inner surface thereof and said rim extension including a foam pad impregnated with an antimicrobial agent lining the inner surface thereof;

b) a second short semicylindrical segment with a semicylindrical rim extension at one end that extends to a diameter larger than said second short semicylindrical segment, said short segment comprising a foam pad lining an inner surface thereof and said rim extension including a foam pad impregnated with an antimicrobial agent lining the inner surface thereof;

c) a web at one edge of each short semicylindrical segment to allow connection of said short semicylindrical segments together to form a central lumen within the foam pads to accommodate the Foley catheter;

d) locking means on the first and second short semicylindrical segments for locking the device in a operative position;

e) A single or multi-layered condom shaped tubular structure attached to the upper end of said rim extension, and;

f) a flexible belt attached to the condom shaped tubular structure, the flexible belt and condom shaped tubular structure acting together to anchor the Foley catheter holder in the urethral meatus.

2. A urethral Foley catheter holder and anchoring device comprising:

a) a first short semi cylindrical segment with a semicylindrical rim extension at one end that extends to a diameter larger than said short semi cylindrical segment, said short segment comprising a foam pad lining an inner surface thereof and said rim extension including a foam pad impregnated with an anti-microbial agent lining the inner surface thereof;

b) a second short semi cylindrical segment with a semicylindrical rim extension at one end that extends to a diameter larger than said second short semi cylindrical segment, said short segment comprising a foam pad lining an inner surface thereof and said rim extension including a foam pad impregnated with an anti-microbial agent lining the inner surface thereof;

c) a web at one edge of each short semi cylindrical segment to allow connection of said short semi cylindrical segments together to form a central lumen within the foam pads to accommodate the Foley catheter;

d) locking means on said first and second short semi cylindrical segments for locking the device in an operative position;

e) a perineal shield attached to said rim extension;

f) a flexible belt attached to the perineal shield.

3. The Foley catheter holder and anchoring device of claim 1, wherein the device further includes a scrotal support behind the condom.

* * * * *